(12) United States Patent
Reicher et al.

(10) Patent No.: US 7,970,625 B2
(45) Date of Patent: Jun. 28, 2011

(54) SYSTEMS AND METHODS FOR RETRIEVAL OF MEDICAL DATA

(75) Inventors: Murray A. Reicher, Rancho Santa Fe, CA (US); Evan K. Fram, Paradise Valley, AZ (US); Steven M. Greim, Oceanside, CA (US); Howard T. Lam, San Diego, CA (US)

(73) Assignee: DR Systems, Inc., San Diego, CA (US)

( * ) Notice: Subject to any disclaimer, the term of this patent is extended or adjusted under 35 U.S.C. 154(b) by 1039 days.

(21) Appl. No.: 11/265,979

(22) Filed: Nov. 3, 2005

(65) Prior Publication Data

US 2006/0095423 A1    May 4, 2006

Related U.S. Application Data

(60) Provisional application No. 60/625,690, filed on Nov. 4, 2004.

(51) Int. Cl.
*G06Q 10/00* (2006.01)
*G06Q 50/00* (2006.01)

(52) U.S. Cl. .......................................................... 705/2

(58) Field of Classification Search .................. 705/2, 4; 707/10; 378/37
See application file for complete search history.

(56) References Cited

U.S. PATENT DOCUMENTS

| | | | |
|---|---|---|---|
| 4,672,683 A | 6/1987 | Matsueda | |
| 5,123,056 A | 6/1992 | Wilson | |
| 5,431,161 A | 7/1995 | Ryals et al. | |
| 5,452,416 A | 9/1995 | Hilton et al. | |
| 5,542,003 A | 7/1996 | Wofford | |
| 5,734,915 A | 3/1998 | Roewer | |
| 5,740,267 A | 4/1998 | Echerer et al. | |
| 5,779,634 A | 7/1998 | Ema et al. | |
| 5,852,646 A | 12/1998 | Klotz et al. | |
| 5,926,568 A | 7/1999 | Chaney et al. | |
| 5,954,650 A | 9/1999 | Saito et al. | |
| 5,976,088 A | 11/1999 | Urbano et al. | |
| 5,987,345 A | 11/1999 | Engelmann et al. | |
| 5,995,644 A | 11/1999 | Lai et al. | |
| 6,115,486 A | 9/2000 | Cantoni | |
| 6,151,581 A | 11/2000 | Kraftson et al. | |
| 6,175,643 B1 | 1/2001 | Lai et al. | |
| 6,185,320 B1 | 2/2001 | Bick et al. | |
| 6,304,667 B1 | 10/2001 | Reitano | |
| 6,347,329 B1 | 2/2002 | Evans | |

(Continued)

OTHER PUBLICATIONS

Crowley, Rebecca et al., *Development of Visual Diagnostic Expertise in Pathology: an Information-processing Study*, Jan. 2003, Journal of the American medical Informatics Association, vol. 10, No. 1, pp. 39-51.

(Continued)

*Primary Examiner* — Gerald J. O'Connor
*Assistant Examiner* — John A Pauls
(74) *Attorney, Agent, or Firm* — Knobbe Martens Olson & Bear, LLP

(57) ABSTRACT

A system and method for transmitting medical data. In one embodiment, a computer system receives filter criteria from a user of a first computer. Furthermore, the computer system may receive schedule information defining a schedule for checking for medical data. Depending on the embodiment, either the computer system or a remote server periodically selects, based upon the received schedule, medical data satisfying the received user-specific rules. The selected medical data is then transmitted to the computer system.

33 Claims, 5 Drawing Sheets

U.S. PATENT DOCUMENTS

| | | | |
|---|---|---|---|
| 6,351,547 | B1 | 2/2002 | Johnson et al. |
| 6,424,996 | B1 | 7/2002 | Killcommons et al. |
| 6,463,169 | B1 | 10/2002 | Ino et al. |
| 6,532,299 | B1 | 3/2003 | Sachdeva et al. |
| 6,532,311 | B1 | 3/2003 | Pritt |
| 6,556,695 | B1 | 4/2003 | Packer et al. |
| 6,563,950 | B1 | 5/2003 | Wiskott et al. |
| 6,574,629 | B1 * | 6/2003 | Cooke et al. ............ 707/10 |
| 6,577,753 | B2 | 6/2003 | Ogawa |
| 6,603,494 | B1 | 8/2003 | Banks et al. |
| 6,630,937 | B2 | 10/2003 | Kallergi et al. |
| 6,678,764 | B2 | 1/2004 | Parvulescu et al. |
| 6,697,506 | B1 | 2/2004 | Oian et al. |
| 6,775,402 | B2 | 8/2004 | Bacus et al. |
| 6,778,689 | B1 | 8/2004 | Aksit et al. |
| 6,820,100 | B2 | 11/2004 | Funahashi |
| 6,829,377 | B2 | 12/2004 | Milioto |
| 6,864,794 | B2 | 3/2005 | Betz |
| 6,886,133 | B2 | 4/2005 | Bailey et al. |
| 6,891,920 | B1 | 5/2005 | Minyard et al. |
| 6,917,696 | B2 | 7/2005 | Soenksen |
| 6,996,205 | B2 | 2/2006 | Capolunghi et al. |
| 7,022,073 | B2 | 4/2006 | Fan et al. |
| 7,027,633 | B2 | 4/2006 | Foran et al. |
| 7,031,846 | B2 | 4/2006 | Kaushikkar et al. |
| 7,043,474 | B2 | 5/2006 | Mojsilovic |
| 7,050,620 | B2 | 5/2006 | Heckman |
| 7,092,572 | B2 | 8/2006 | Huang et al. |
| 7,103,205 | B2 | 9/2006 | Wang et al. |
| 7,106,479 | B2 | 9/2006 | Roy et al. |
| 7,110,616 | B2 | 9/2006 | Ditt et al. |
| 7,149,334 | B2 | 12/2006 | Dehmeshki |
| 7,155,043 | B2 | 12/2006 | Daw |
| 7,170,532 | B2 | 1/2007 | Sako |
| 7,174,054 | B2 | 2/2007 | Manber et al. |
| 7,209,149 | B2 | 4/2007 | Jogo |
| 7,212,661 | B2 | 5/2007 | Samara et al. |
| 7,218,763 | B2 | 5/2007 | Belykh et al. |
| 7,224,852 | B2 | 5/2007 | Lipton et al. |
| 7,260,249 | B2 | 8/2007 | Smith |
| 7,263,710 | B1 | 8/2007 | Hummel, Jr. et al. |
| 7,272,610 | B2 | 9/2007 | Torres |
| 7,412,111 | B2 | 8/2008 | Battle et al. |
| 7,450,747 | B2 | 11/2008 | Jabri et al. |
| 7,526,114 | B2 | 4/2009 | Seul et al. |
| 7,545,965 | B2 | 6/2009 | Suzuki et al. |
| 7,583,861 | B2 | 9/2009 | Hanna et al. |
| 7,613,335 | B2 | 11/2009 | McLennan et al. |
| 7,634,121 | B2 | 12/2009 | Novatzky et al. |
| 7,636,413 | B2 | 12/2009 | Toth |
| 7,660,488 | B2 | 2/2010 | Reicher et al. |
| 7,787,672 | B2 | 8/2010 | Reicher et al. |
| 7,885,440 | B2 | 2/2011 | Fram et al. |
| 7,920,152 | B2 | 4/2011 | Fram et al. |
| 2002/0016718 | A1 * | 2/2002 | Rothschild et al. ........... 705/2 |
| 2002/0021828 | A1 | 2/2002 | Papier et al. |
| 2002/0044696 | A1 | 4/2002 | Sirohey et al. |
| 2002/0081039 | A1 | 6/2002 | Funahashi |
| 2002/0091659 | A1 | 7/2002 | Beaulieu et al. |
| 2002/0103673 | A1 | 8/2002 | Atwood |
| 2002/0103827 | A1 | 8/2002 | Sesek |
| 2002/0106119 | A1 | 8/2002 | Foran et al. |
| 2002/0110285 | A1 | 8/2002 | Wang et al. |
| 2002/0164063 | A1 | 11/2002 | Heckman |
| 2002/0188637 | A1 | 12/2002 | Bailey et al. |
| 2003/0028402 | A1 | 2/2003 | Ulrich et al. |
| 2003/0036087 | A1 | 2/2003 | Kaushikkar et al. |
| 2003/0053668 | A1 | 3/2003 | Ditt et al. |
| 2003/0065613 | A1 | 4/2003 | Smith |
| 2003/0115083 | A1 | 6/2003 | Masarie et al. |
| 2003/0123717 | A1 | 7/2003 | Bacus et al. |
| 2003/0185446 | A1 | 10/2003 | Huang et al. |
| 2003/0195416 | A1 | 10/2003 | Toth |
| 2004/0008900 | A1 | 1/2004 | Jabri et al. |
| 2004/0024303 | A1 | 2/2004 | Banks et al. |
| 2004/0086163 | A1 | 5/2004 | Moriyama et al. |
| 2004/0088192 | A1 | 5/2004 | Schmidt et al. |
| 2004/0101191 | A1 | 5/2004 | Seul et al. |
| 2004/0114714 | A1 * | 6/2004 | Minyard et al. ............ 378/37 |
| 2004/0141661 | A1 | 7/2004 | Hanna et al. |
| 2004/0151374 | A1 | 8/2004 | Lipton et al. |
| 2004/0161139 | A1 | 8/2004 | Samara et al. |
| 2004/0161164 | A1 | 8/2004 | Dewaele |
| 2004/0165791 | A1 | 8/2004 | Kaltanji |
| 2004/0170312 | A1 | 9/2004 | Soenksen |
| 2004/0197015 | A1 | 10/2004 | Fan et al. |
| 2004/0243435 | A1 | 12/2004 | Williams |
| 2004/0254816 | A1 | 12/2004 | Myers |
| 2004/0264753 | A1 | 12/2004 | Capolunghi et al. |
| 2005/0027570 | A1 | 2/2005 | Maier et al. |
| 2005/0036668 | A1 | 2/2005 | McLennan et al. |
| 2005/0043970 | A1 | 2/2005 | Hsieh |
| 2005/0063612 | A1 | 3/2005 | Manber et al. |
| 2005/0065424 | A1 | 3/2005 | Shah et al. |
| 2005/0114178 | A1 | 5/2005 | Krishnamurthy et al. |
| 2005/0114179 | A1 | 5/2005 | Brackett et al. |
| 2005/0114283 | A1 | 5/2005 | Pearson et al. |
| 2005/0184988 | A1 | 8/2005 | Yanof et al. |
| 2005/0197860 | A1 | 9/2005 | Joffe et al. |
| 2005/0273009 | A1 | 12/2005 | Deischinger et al. |
| 2006/0093198 | A1 | 5/2006 | Fram et al. |
| 2006/0093199 | A1 | 5/2006 | Fram et al. |
| 2006/0093207 | A1 | 5/2006 | Reicher et al. |
| 2006/0095426 | A1 | 5/2006 | Takachio et al. |
| 2006/0106642 | A1 | 5/2006 | Reicher et al. |
| 2006/0111941 | A1 | 5/2006 | Blom |
| 2006/0181548 | A1 | 8/2006 | Hafey et al. |
| 2006/0239573 | A1 | 10/2006 | Novatzky et al. |
| 2007/0050701 | A1 | 3/2007 | El Emam et al. |
| 2007/0055550 | A1 | 3/2007 | Courtney et al. |
| 2007/0067124 | A1 | 3/2007 | Kimpe et al. |
| 2007/0073556 | A1 | 3/2007 | Lau et al. |
| 2007/0174079 | A1 | 7/2007 | Kraus |
| 2007/0239481 | A1 | 10/2007 | DiSilvestro et al. |
| 2008/0103828 | A1 | 5/2008 | Squilla et al. |
| 2010/0138239 | A1 | 6/2010 | Reicher et al. |
| 2010/0198608 | A1 | 8/2010 | Kaboff et al. |
| 2010/0201714 | A1 | 8/2010 | Reicher |
| 2011/0016430 | A1 | 1/2011 | Fram et al. |

OTHER PUBLICATIONS

Non-Final Office Action dated Aug. 28, 2007 in U.S. Appl. No. 11/179,384.

Jan. 17, 2008 Response to Non-Final Office Action dated Aug. 28, 2007 in U.S. Appl. No. 11/179,384.

Final Office Action dated Jun. 26, 2008 in U.S. Appl. No. 11/179,384.

Non-Final Office Action dated Jul. 27, 2009 in U.S. Appl. No. 11/265,978.

Non-Final Office Action dated Aug. 24, 2009 in U.S. Appl. No. 11/268,262.

Non-Final Office Action dated Dec. 29, 2008 in U.S. Appl. No. 11/179,384.

Final Office Action dated Jul. 24, 2009, in U.S. Appl. No. 11/179,384.

Non-Final Office Action dated Oct. 1, 2009, in U.S. Appl. No. 11/268,261.

Notice of Allowance dated Feb. 2, 2010 in U.S. Appl. No. 11/268,261.

Notice of Allowance dated Nov. 19, 2009 in U.S. Appl. No. 11/265,978.

Notice of Allowance, dated Apr. 19, 2010 in U.S. Appl. No. 11/265,978.

Notice of Allowance, dated Nov. 3, 2009 in U.S. Appl. No. 11/179,384.

Non-Final Office Action dated Apr. 14, 2010 in U.S. Appl. No. 11/944,027.

Non-Final Office Action dated Apr. 16, 2010 in U.S. Appl. No. 11/268,262.

Notice of Allowance dated May 17, 2010, in U.S. Appl. No. 11/268,261.

Supplemental Notice of Allowance dated May 3, 2010 in U.S. Appl. No. 11/265,978.

Non-Final Office Action dated May 26, 2010 in U.S. Appl. No. 11/942,673.

Supplemental Notice of Allowance dated Aug. 6, 2010, in U.S. Appl. No. 11/268,261.
Supplemental Notice of Allowance dated Aug. 3, 2010 in U.S. Appl. No. 11/265,978.
Interview Summary dated May 14, 2010, in U.S. Appl. No. 11/268,261.
Interview Summary dated Mar. 4, 2010 in U.S. Appl. No. 11/265,979.
Interview Summary dated Nov. 24, 2009 in U.S. Appl. No. 11/268,262.
Interview Summary dated May 12, 2010 in U.S. Appl. No. 11/268,262.
Interview Summary dated Jul. 26, 2010 in U.S. Appl. No. 11/942,673.
Interview Summary dated May 13, 2010 in U.S. Appl. No. 11/944,027.
Non-Final Office Action dated Aug. 18, 2010 in U.S. Appl. No. 12/702,976.
Notice of Allowance dated Oct. 8, 2010, in U.S. Appl. No. 11/268,261.
Final Office Action dated Oct. 28, 2010 in U.S. Appl. No. 11/268,262.
NonFinal Office Action dated Sep. 16, 2010 in U.S. Appl. No. 11/942,687.
Non-Final Office Action dated Sep. 29, 2010 in U.S. Appl. No. 11/944,000.
Interview Summary dated Dec. 1, 2010, 2010 in U.S. Appl. No. 12/702,976.
Notice of Allowance dated Dec. 3, 2010, in U.S. Appl. No. 11/268,261.
Notice of Allowance dated Jan. 6, 2011, in U.S. Appl. No. 11/268,261.
Interview Summary dated Dec. 1, 2010 in U.S. Appl. No. 11/268,262.
Notice of Allowance dated Dec. 1, 2010 in U.S. Appl. No. 11/268,262.
Final Office Action dated Nov. 26, 2010 in U.S. Appl. No. 11/942,673.
Interview Summary dated Dec. 3, 2010 in U.S. Appl. No. 11/942,687.
Final Office Action dated Dec. 23, 2010 in U.S. Appl. No. 11/944,027.
Final Office Action dated Feb. 17, 2011 in U.S. Appl. No. 12/702,976.
Notice of Allowance dated Feb. 25, 2011 in U.S. Appl. No. 11/268,262.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Final Office Action, dated Apr. 5, 2011 in U.S. Appl. No. 11/942,687.
Interview Summary dated Mar. 31, 2011 in U.S. Appl. No. 11/944,027.
Final Office Action dated Apr. 20, 2011 in U.S. Appl. No. 11/944,000.
Non-Final Office Action dated May 5, 2011 in U.S. Appl. No. 12/870,645.
Office Action dated May 16, 2011, in U.S. Appl. No. 12/857,915.
US 7,801,341, 09/2010, Fram et al. (withdrawn)

* cited by examiner

| Exams that meet Receivable Exam Criteria | | | | | | | | | | | |
|---|---|---|---|---|---|---|---|---|---|---|---|
| Patient ID | Site | Last Name | First Name | Sex | Age | Exam Date | Time | Mod | Exam Description | Status | Received | Completed |
| 20020003007 | DRS | LIVER | LAURA | F | 55 | 01/18/2005 | 12:13 | NM | CARD AD PR R S 1 SD | S | 100% | Yes |
| 20020003007 | DRS | LIVER | LAURA | F | 55 | 01/18/2005 | 12:31 | NM | CARD AD PR R S 1 SD | S | 100% | No |
| 20020003007 | DRS | LIVER | LAURA | F | 55 | 01/18/2005 | 12:36 | NM | CARD AD PR R S 1 SD | S | 100% | Yes |
| 58777 | DRS | WILLIAMS | CHARLES' | M | 16 | 01/21/2005 | 15:42 | MR | ABDOMEN | S | 100% | No |
| 685474 | DRS | WILLIAMS | CHARLES' | M | 11 | 01/21/2005 | 13:13 | NM | LUNG VQ SETTING | S | 52% | No |
| 685474 | DRS | WILLIAMS | CHARLES' | M | 11 | 01/21/2005 | 15:45 | CT | CTA - CIRCLE OF WILLIS | S | 50% | No |

Receive options...   Select All   Receive   Close

SYSTEMS AND METHODS FOR RETRIEVAL OF MEDICAL DATA

CROSS-REFERENCE TO RELATED APPLICATIONS

This application claims priority under 35 U.S.C. §119(e) to U.S. Provisional Application Ser. No. 60/625,690, filed on Nov. 4, 2004, which is hereby expressly incorporated by reference in its entirety.

BACKGROUND OF THE INVENTION

1. Field of the Invention

This invention relates to management and retrieval of medical images.

2. Description of the Related Art

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. In addition, many imaging modalities are inherently digital, such as MRI, CT, nuclear medicine, and ultrasound. Increasingly these digital images are viewed, manipulated, and interpreted using computers and related computer equipment. Accordingly, there is a need for improved systems and methods of viewing and retrieving these digital images.

SUMMARY OF THE INVENTION

One embodiment comprises a method of retrieving medical data. The method comprises receiving user-specific rules from a user of a first computer. The user specific rules define criteria for exams to be retrieved by the first computer. The method also comprises receiving schedule information defining a schedule for checking for medical data and periodically selecting, based upon the received schedule, medical data satisfying the user-specific rules. In one embodiment, the selected medical data is retrieved from a second computer.

Another embodiment includes a system for retrieving medical data, the system comprises: a central processing unit; and an application module executing on the central processing unit, wherein the application module receives user-specific rules and an update schedule. The application module periodically selects medical data satisfying the received user-specific rules based upon the update schedule, and wherein the application module retrieves the selected medical data from a remote computer via a network.

BRIEF DESCRIPTION OF THE DRAWINGS

FIG. 5 is an exemplary graphical screen display that identifies for a user which documents have been transmitted to the computing system of FIG. 1.

DETAILED DESCRIPTION OF EMBODIMENTS OF THE INVENTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

One embodiment provides a computing system 100 for receiving and accessing medical related images and documents. In one embodiment the computing system 100 receives medical data from a remote computer, such as an imaging device 170, an image server 180, or other computing system at a medical facility 190. In one embodiment, if there is new information created by these devices, it is periodically downloaded to the computing system 100 based upon a user-specific rules and update schedule.

In one embodiment, the computing system 100 can be left unattended in "auto-receive" mode. This means that a user, such as a physician, typically will not have to wait for exams to download; the exams they are interested in will be available when the user accesses the computing system 100.

In one embodiment, as will be discussed further below, the user will be able to provide a set of rules ("auto-receive criteria") that determines which exams should be auto-received. For instance, the user may wish to only receive "MRI" exams. In one embodiment, authorization criteria set by an administrator can impose limits on the range or types of auto-receive criteria that can be specified. This may be beneficial to preserve patient confidentiality, as well as to control network congestion. For example, in one embodiment, a user can only specify exams for which he is one of the listed referring doctors. Another criteria can include that a user cannot auto-receive exams that are more than 2 weeks old.

In one embodiment, once information is auto-retrieved, an interface is provided that allows a user to mark the information as being "completed" or "reviewed." The "completed" or other such status marker may be visible in an exam grid that is displayed on a display connected to the computing system 100. This makes it easy for the user to track which retrieved information has been viewed. In one embodiment, the computing system 100 stores this information beyond the deletion of the exam so that an already-completed document will not be auto-received a second time.

Figure 1:
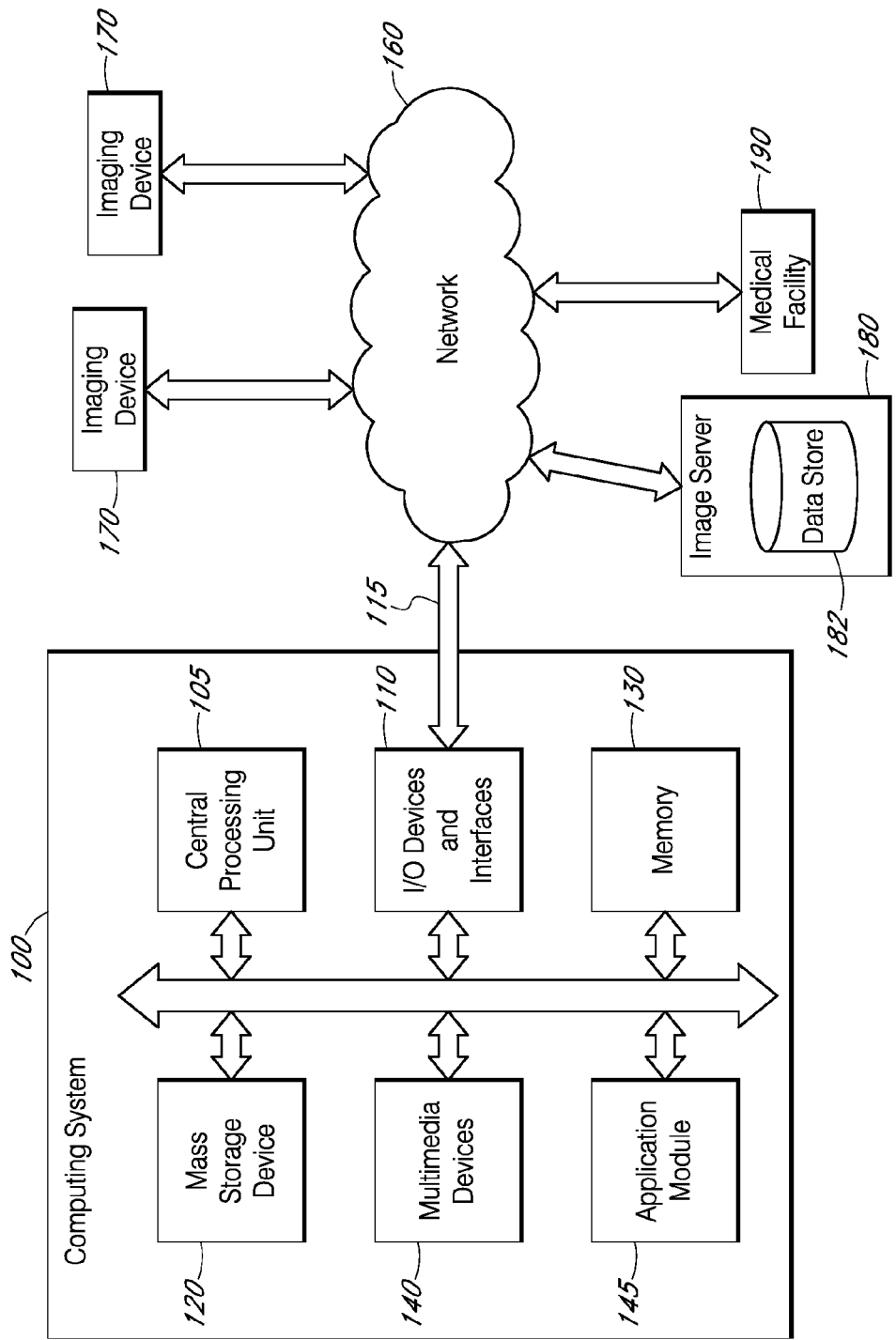
FIG. 1 is a block diagram of an exemplary computing system in communication with a network and various networked devices.

FIG. 1 is a block diagram of the computing system 100 in communication with a network 160 and various network devices. The computing system 100 may be used to implement certain systems and methods described herein. The functionality provided for in the components and modules of computing system 100 may be combined into fewer components and modules or further separated into additional components and modules.

In one embodiment, once information is auto-retrieved, an interface is provided that allows a user to mark the information as being "completed" or "reviewed." When reading is complete, an exam may be labeled "read," indicating that the medical professional has completed observation of the one or more medical images for purposes of creating a medical report. The "completed" or other such status marker may be visible in an exam grid that is displayed on a display connected to the computing system 100. This makes it easy for the user to track which retrieved information has been viewed. In one embodiment, the computing system 100 stores this information beyond the deletion of the exam so that an already-completed document will not be auto-received a second time.

The computing system 100 further includes a memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing system 100 is generally controlled and coordinated by operating system software, such as the Windows 95, 98, NT, 2000, XP or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing system 100 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images may be displayed. According to the systems and methods described below, medical images may be stored on the computing system 100 or another device that is local or remote, displayed on a display device, and manipulated by the application module 145. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is coupled to a network 160, such as a LAN, WAN, or the Internet, for example, via a communication link 115. The network 160 may be coupled to various computing devices and/or other electronic devices. In the exemplary embodiment of FIG. 1, the network 160 is coupled to imaging devices 170, an image server 180, and a medical facility 190. In addition to the devices that are illustrated in FIG. 1, the network 160 may communicate with other computing, imaging, and storage devices.

The imaging devices 170 may be any type of device that is capable of acquiring medical images, such as an MRI, x-ray, mammography, or CT scan systems. The image server 180 includes a data store 182 that is configured to store images and data associated with images. In one embodiment, the imaging devices 170 communicate with the image server 182 via the network 160 and image information is transmitted to the image server 180 and stored in the data store 182. In one embodiment, the image data is stored in Digital Imaging and Communications in Medicine ("DICOM") format. The complete DICOM specifications may be found on the National Electrical Manufactures Association Website. Also, NEMA PS 3 —*Digital Imaging and Communications in Medicine,* 2004 ed., Global Engineering Documents, Englewood CO, 2004, provides an overview of the DICOM standard. Each of the above-cited references is hereby incorporated by reference in their entireties. In one embodiment, the data store 182 also stores the user-specific rules and an update schedule for determining when to search for new "medical data" to transmit to the computing system 100. As discussed in further detail below, the user-specific rules may vary depending upon user, type of application, or other factors.

"Medical data" is defined to include any data related to medical information, images, and patient information. As non-limiting examples, it may include but is not limited to a radiograph, computed tomography (CT), magnetic resonance imaging (MRI), Ultrasound (US), mammogram, positron emission tomography scan (PET), nuclear scan (NM), pathology, endoscopy, text files containing reports, voice files with results summaries, full digital dictation voice files for transcription, ophthalmology, or many other types of medical images. While this description is directed to retrieving and viewing of medical images, the methods and systems described herein may also be used in conjunction with non-medical images, such as, images of circuit boards, airplane wings, and satellite images, for example.

The exemplary image server 180 is configured to store images from multiple sources and in multiple formats. For example, the image server 180 may be configured to receive medical images in the DICOM format from multiple sources, store these images in the data store 182, and selectively transmit medical images to requesting computing devices.

The medical facility 190 may be a hospital, clinic, doctor's office, or any other medical facility. The medical facility 190 may include one or more imaging devices and may share medical images with the image server 180 or other authorized computing devices. In one embodiment, multiple computing systems, such as the computing system 100 may be housed at a medical facility, such as medical facility 190.

Figure 2:
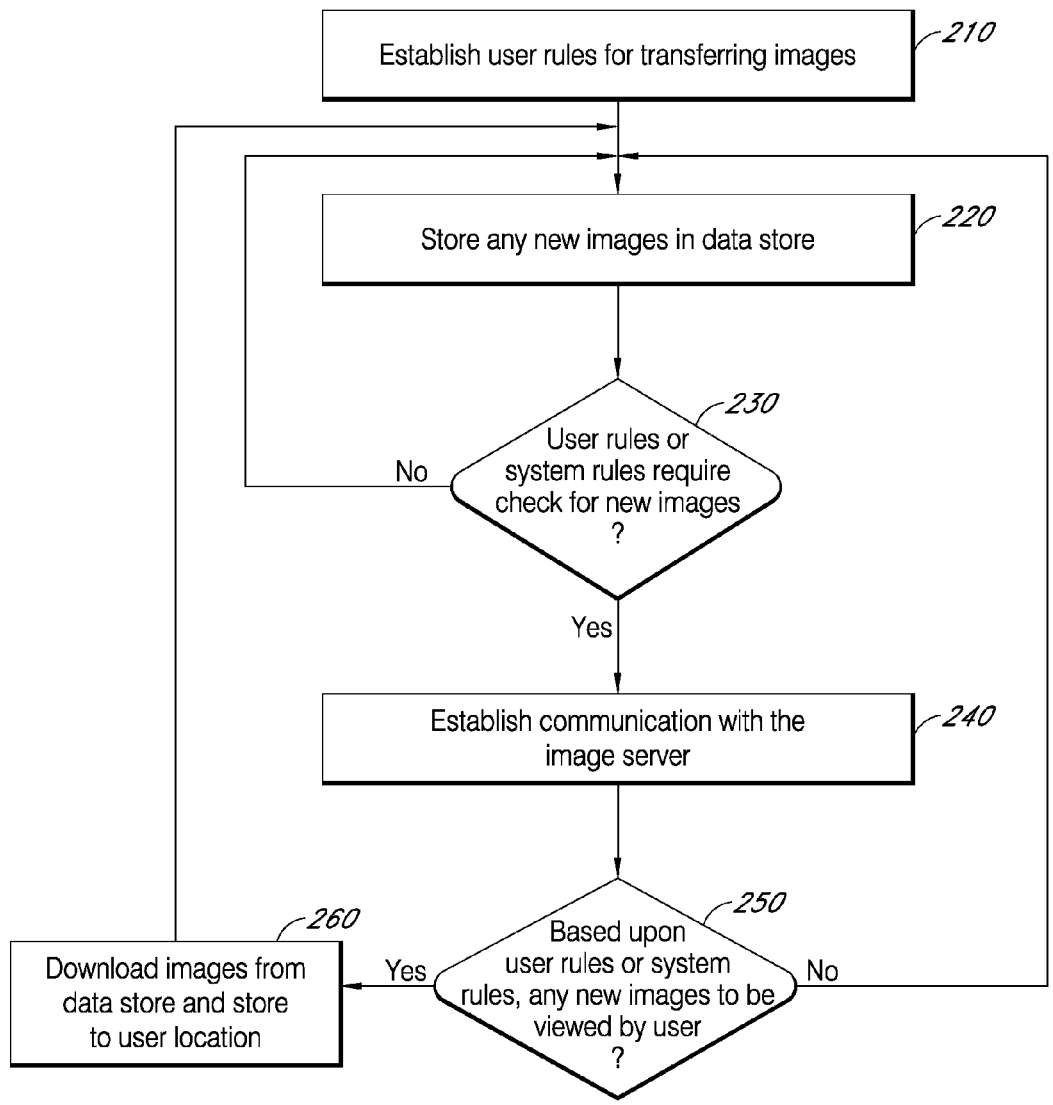
FIG. 2 is a flowchart illustrating a method of retrieving documents from a remote location based upon user-provided criteria.

FIG. 2 is a flowchart illustrating a method for transferring image data, wherein images are automatically retrieved based on user preferences. FIG. 2 illustrates an exemplary method for automatic transfer of medical images from the image server 180 to the medical facility 190 or to the computing system 100. As those of skill in art may appreciate, medical images are often high resolution, and thus, may require significant time to transfer from an imaging device or image storage device to the user's computing system. As described in further detail below, a user may establish a user specific set of rules that will determine how often the image server 180 is queried and which types of exams will be transmitted. Criteria may include, for example, the exam type, modality, time of day, and exam status. It is noted that the method of FIG. 2 can be controlled by doctors, their staff, transcriptionists, billers, and others.

With respect to FIG. 1, for example, images from multiple imaging devices 170 and facilities 190 may be stored on the data store 182 at image server 180. These images stored at the image server 180 may be marked for viewing by a remote user, such as by a doctor operating the computing system 100. Accordingly, the computing system 100 should, at some point prior to displaying the images stored on the image server 180, download the images to the mass storage device 120 of the computing system 100, for example. If a large number of images are marked for viewing by the user of the computing system 100, transfer of this large number of images may require a substantial amount of time. Accordingly, FIG. 2 provides an exemplary method for automatically transferring images to a desired computing system for later viewing.

It is noted that although FIG. 2 is directed to a process of downloading medical data directly to the computing system 100. In another embodiment, the medical data may be transmitted from a network 160 to a data store on a smaller network, e.g., which is quickly accessible by any of the computers on the network.

In a block 210, rules are established for transfer of images to various computing systems. In one embodiment, these rules comprise general system rules, and specific user rules for each reader, viewer, or user type. The rules may include criteria, or combinations of criteria, such as, time of day, date, physician name, exam type, modality, and various exams statuses, for example. As will be described in further detail below, these rules establish criteria for downloading images to specific computing systems. In one embodiment, general system rules are established and are used in the absence of specific user rules.

Figure 4:
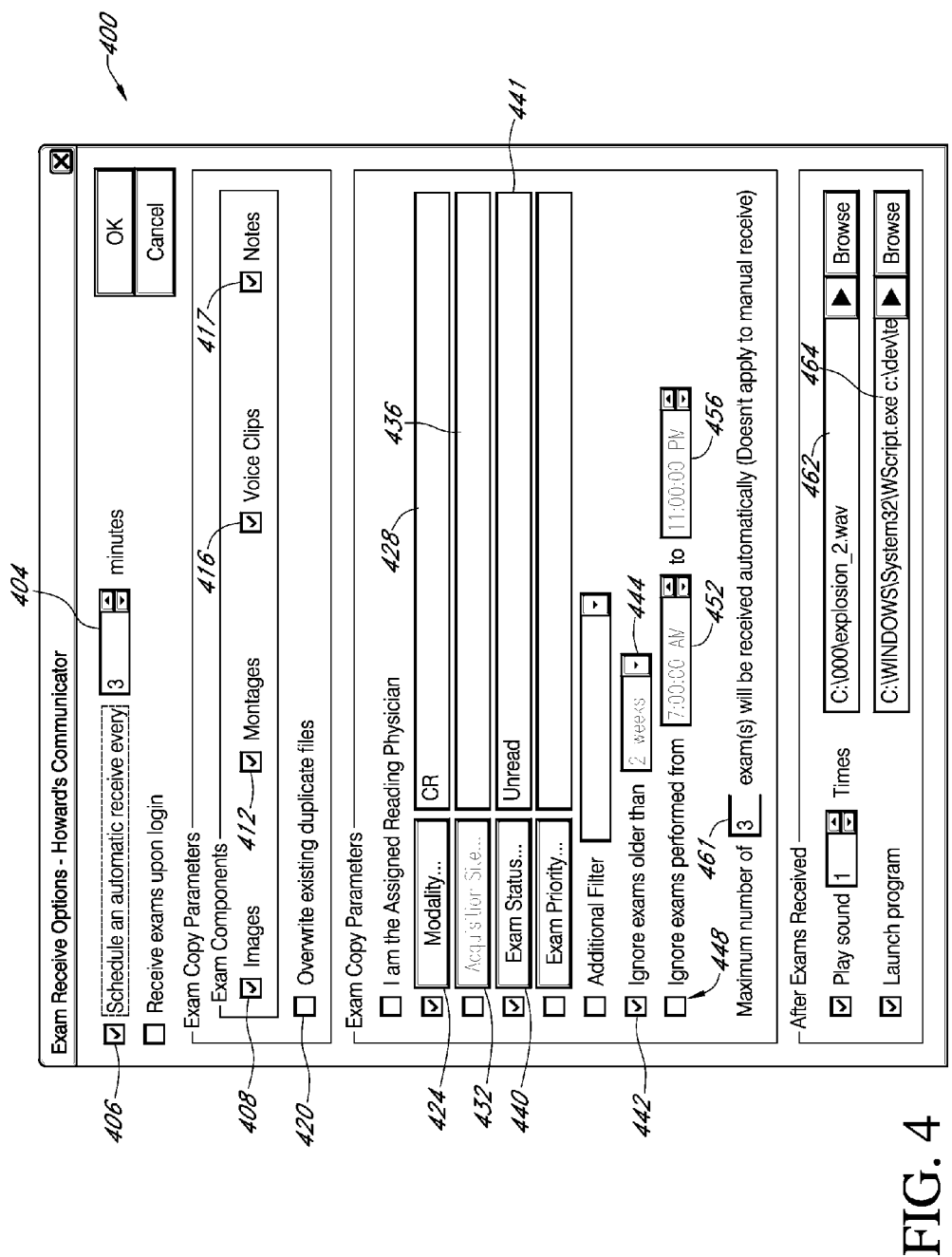
FIG. 4 is an exemplary graphical user interface that allows a user to define certain auto-receive criteria.

The rules established in block 210 may indicate that the image server 180 should be checked for new images every hour, for example. The rules may further indicate that, upon identifying images on the image server for listed patients, the images should be immediately downloaded to the reader's or viewer's computing system and stored on a mass storage device for later review by the physician, for example. In another embodiment, the rules may indicate that images with certain keywords in their file names should be downloaded, while any remaining images should not be downloaded. In another embodiment, the rules indicate that images are downloaded based on the imaging modality, and/or time of day acquired, and/or referring physician, and/or physician who performed the procedure, and/or user type, or other criteria. Accordingly, the rules may include both criteria for checking for new images and criteria for downloading new images. FIG. 4 illustrates a graphical specifying certain exemplary rules that may be defined by a user.

Continuing to a block 220, new images are stored in the data store 182 of the image server 180. As described above, these images may be received from countless image sources, including the imaging devices 170, the medical facility 190, and other medical imaging sources. In one embodiment, the image server 180 includes software and/or hardware that renames medical data.

Moving to a decision block 230, the computing device 100 determines if the rules require a check for new images on the image server 180. For example, a particular user rule may establish that a communication link with the image server 180 is established every day at 3:00 PM. Accordingly, as illustrated in FIG. 5, the decision block 230 continues to loop with block 220 until 3:00 PM each day. If block 230 determines that a check for new images is necessary, such as at 3:00 PM each day, for example, the method proceeds to a block 240.

At a block 240, a communication link is established with the image server 180 and the computing system 100 (or another computer that is locally networked to the computing system 100). In one embodiment, the image server 180 comprises multiple servers and other computing devices at multiple locations, where each of the servers and computing devices is in data communication with the network 160. Thus, at block 240, the communication link may be established between the computing system 100 and any other computing device that stores medical images. In one embodiment, the computing system 100 may periodically poll the imaging server 180 to determine if there is new medical data. In another embodiment, the communication link is initiated by the image server 180. In this embodiment, the communication link may be initiated only if there is new medical data satisfying the user-provided rules.

Moving to a decision block 250, the computing system 100 and/or the image server 180 determine if images are present on the image server 180 that should be downloaded to the computing system 100, based on the user rules and/or system rules. For example, if a user rule includes criteria selecting all images of specific patients that are stored on the image server 180, these images should be downloaded to the computing system 100. In another embodiment, if no user rules are established for a particular computing system 100, or a particular user of the computing system 100, the system rules may be applied in determining whether any images stored on the image server 180 should be downloaded to the computing system 100. For example, a system rule may include criteria indicating that only those images that are specifically marked for viewing by a particular user should be downloaded to that user's computing system 100.

It is desirable to allow a user or automated process with access to the image server 180 to explicitly mark cases for downloading by a particular machine, for example one serving a particular group of doctors, or by a particular physician. This could be accomplished by including fields in a database of exams on the image server 180 with this information. When a remote computer connects to the image server 180 to poll for exams to download, it would then download exams that had been marked for download by either that specific machine or exams that were marked for download by the physician logged into that machine. Optionally, the image server 180 could track when the exam had been successfully downloaded and viewed so that the exam would not be downloaded again when the user logged into a different machine.

If in the decision block 250, the computing system 100 and/or image server 180 determine that there are no images stored on the image server 180 that are to be transferred to the computing system 100, the method continues to block 220, where new images are stored in the mass storage device 120.

In the decision block 250, if it is determined that there are images stored on the server 180 that are to be transferred to the computing system 100, the method continues to block 260, where the images are transferred from the data store 182 to the computing system 100. If, for example, multiple images are transferred from the image server 182 to the computing system 100, significant time may be required for this transfer. Accordingly, by establishing rules that download images prior to the user's anticipated viewing time, the user may not be required to wait for the images to transfer from the image server 182 the computing system 100.

Figure 3:
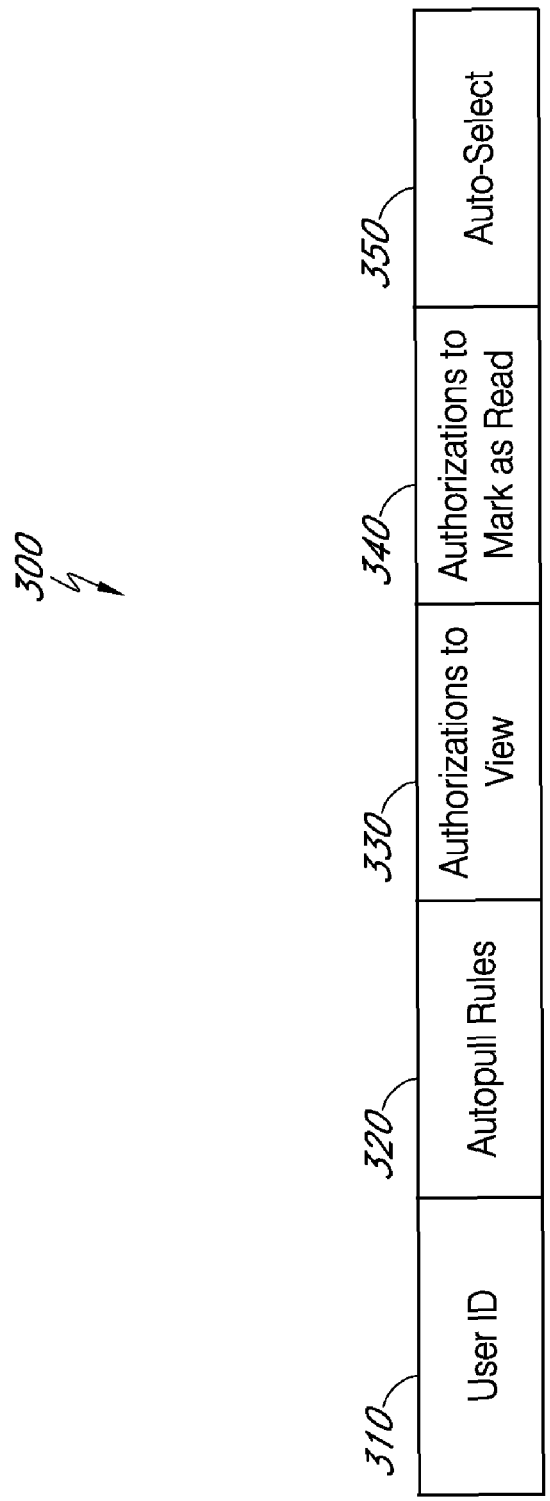
FIG. 3 is a block diagram illustrating an exemplary record that may be maintained with respect to the system of FIG. 1.

FIG. 3 illustrates an exemplary data rule data structure 300 that may be used to define the user-rules. The rule data structure 300 may be stored in a database. Depending on the embodiment, the rule data structure 300 may be located at the computing system 100 if the system is "pull driven," i.e., the computing system 100 polls a remote device to determine the availability of medical data. Alternatively, the rule data structure 300 may be located at the image server 180 if the system is "push driven," i.e., the image server 180 periodically determines whether to transmit data to the computing system 100. As is shown in FIG. 3, each user is assigned a user ID 310, which is recorded as a portion of the rule data structure 300. In one embodiment, the user ID 310 is an abbreviation of the user's name or a combination of the user's name and other text of characters. The exemplary data structure 300 includes auto-pull rules 320, which indicate the user's preferences for monitoring and downloading exams from remote computing devices, such as from the image server 380, for example. The auto-pull rules 320 may be in any known format, and may include various criteria for monitoring and transmitting image files. See the description of FIG. 2 for further discussion regarding generation and application of these rules. In addition to the above, the auto-pull rules 320 may established to retrieved medical data based upon any of the following criteria: modality (MRI, CT, X-ray etc); exam type (left knee X-ray, CT Chest, MRI Brain etc); notes type attached to exam (teaching note, ER note, quality assessment note, technologist note, scheduling note, etc); transcriptionist; exam priority (e.g., STAT, ASAP, LOW); ordered from (i.e., ordered from the emergency room, ICU); acquisition site (e.g. acquired at hospital #1 or imaging center #2); exam status (e.g., has the exam been read); archive status (has the exam been archived, archived and restored, not yet archived); assigned physician (has the exam been assigned to a particular physician for interpretation); reading physician (which doctor read the exam), ABN (ABN stands for advanced beneficiary notice—some exams may be marked because an ABN form is required from the patient), exam age (how long ago was the exam done); patient age; medical necessity (is the exam marked to indicate that a medical necessity is required); check-in-status (has the patient checked into the department—a record might exist even before images are acquired); confirmation required (a record can be created before an exam is performed—this criteria indicates that the exam has been marked to indicate that the patient should be called to confirm the exam); eligibility (this marker indicates whether insurance eligibility has been established); report status (has a text report been generated, transcribed, approved or other statuses); and report actions (has the completed report been faxed, stored, sent out to other systems).

Each of the foregoing filter criteria may be selected using simple or complex search expressions such "AND" or "OR." Complex filter criteria may be stored on the image server 180, then used by local devices that access these records via the web.

The authorizations to view rules 330 include criteria for determining which exams the user may view. For example, the authorizations to view rules 330 field for a hospital administrator may indicate that the administrator can view any exam stored on a computing device stored in the hospital or generated at the hospital.

The authorizations to mark as read rules 340 include criteria for determining if the user has rights to mark an exam as read. As discussed above, only authorized users should be allowed to mark an exam as read. Accordingly, using the exemplary data structure of FIG. 3, each user may be given specific rights to mark exams as read. For example, a MRI or x-ray technician may not have any rights to mark exams as read. However, a doctor may have rights to mark as read certain exam types.

The auto select rules 350 include criteria for automatically selecting related images for retrieval, based upon a current image that is viewed by the user. As non-limiting examples, a user may define a rule to retrieve any medical data that meets the following criteria: the medical data is created a certain day and/or time period, the medical data is stored in a particular location, and/or the medical data is related to a type of exam. Thus, in one embodiment, if the user is viewing selected medical data, other medical data is automatically retrieved from the image server 180 via the network 160 to the computing system 100. The retrieved medical data is selected based upon user-specific rules.

The authorizations to mark as read rules 340 include criteria for determining if the user has rights to mark an exam as read. As discussed above, only authorized users should be allowed to mark an exam as read. In one embodiment, marking an exam as read indicates that the viewer has completed his review and evaluation of the exam. As those of skill in the art will recognize, if an exam is improperly notated as read, the physician, or other user, may not properly review the exam. Thus, ensuring that only authorized users are allowed to mark an exam as read reduces the likelihood that a physician fails to view an exam or inadvertently marks as read an examination he is authorized to view but not mark as read. Accordingly, using the exemplary data structure of FIG. 3, each user may be given specific rights to mark exams as read. For example, a MRI or x-ray technician may not have any rights to mark exams as read. However, a doctor may have rights to mark as read certain exam types.

FIG. 4 is an exemplary graphical user interface 400 that may be used to receive auto-receive criteria from a physician. Depending on the embodiment, the layout of the graphical user interface, the types of input fields, buttons, and checkboxes may be modified.

Using the graphical user interface 400, a user may input a polling period in input window 404. The user may selectively enable and disable the auto-receive process via the use of checkbox 406. The user can select the types of files to be downloaded as well via checkbox 408 (images), checkbox 412 (montages), checkbox 416 (voice clips), and checkbox 417 (notes). The graphical user interface 400 could also be adapted to identify other types of information such as reports. The checkbox 420 allows a user overwrite duplicate files that may be retrieved if it is checked. A modality button 424 allows a user designate one or more modality criteria. In one embodiment, upon selection of the modality button 424, a pop-up screen illustrating all of the selectable modalities are displayed. Once selected, the designated modalities are displayed in a modality window 428. In one embodiment, the user may input a modality directly into the modality window 428.

In one embodiment, an acquisition site button 432 can be used to allow a user to identify the source of the auto-received information. In one embodiment, upon selection of the acquisition site button 432, a list of authorized locations are presented for user selection. After selection, the selected location is displayed in a location window 436. In one embodiment, an administrator can disable this function for selected users and may designate for a user or a group of users a predefined source location.

Furthermore, the user can identify which information should be retrieved based upon an "exam status" that is associated with the information to be retrieved, e.g., "read", "unread" or "either." In one embodiment, upon selection of an exam status button 440, a list of status types are presented for user selection. After selection, the selected types are displayed in a type window 441. In one embodiment, the user may input a selected status into the type window 441.

Using checkbox 442, a user can request to only receive information that has been generated within a predefined window of time up to the present day. The predefined window of time can be set by a user via the use of input window 444. Moreover, using checkbox 448, a user can select to auto-receive information that was created during a certain period of the day. The user can set the window of time via the use of input fields 452 (to provide a start time) and input field 456 (to provide an end time). Using an input field 461, the user can specify a maximum number of exams to be retrieved automatically.

Furthermore, using input fields 462 and 464, the user can designate the filename of an audio file to be played or a program to be executed. If an audio file is listed, the computing system 100 will play the audio file once information has been retrieved in accordance with the auto-receive criteria. If the user identified a program, it is executed after information has been auto-received. The program can make an audible alert or alternatively send an electronic message ("e-mail") to the user.

FIG. 5 is a screen display 500 illustrating an exemplary graphical user interface that may be used to show a user what documents have been received. In one embodiment, the screen display 500 illustrates which files have been "completed", i.e., reviewed by the user (see "completed" column). Furthermore, the screen display 500 shows what portion of the documents have been "received" via the network 160 (see "received" column). In one embodiment, the completed or receive status may alternatively be shown by check mark, highlight, or other image marking proximate to or on the respective record.

The foregoing description details certain embodiments of the invention. It will be appreciated, however, that no matter how detailed the foregoing appears in text, the invention can be practiced in many ways. For example, the above-described auto-retrieve may be performed on other types of images, in addition to medical images. For example, images of circuit boards, airplane wings, and satellite imagery may be analyzed using the described systems. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of retrieving medical data, the method comprising:
   determining, by a user computing device, based on a user's stored rights to mark respective medical data as read, qualifications of the user of the user computing device to mark medical data as read, wherein users have varying rights to mark different types of medical data as read based on at least their respective medical training, and wherein marking respective medical data as read indicates that the user has completed observation of the respective medical data for purposes of creating a medical report;
   receiving, at the user computing device, user-specific rules from the user defining criteria for medical data to be retrieved by the user computing device;
   periodically selecting any medical data that both satisfies the user-specific rules and is associated with an indication that the medical data has not previously been marked as read by a user that is qualified to mark the respective medical data as read; and
   initiating transfer of the selected medical data for review by the user;
   allowing, by the user computing device, the user to mark the selected medical data as read in accordance with at least the determined qualifications of the user and a type of the selected medical data; and
   transmitting, by the user computing device, read indications received from the user to a network-connected computing device.

2. The method of claim 1, wherein one of the user-specific rules indicates that only medical data assigned to the user is to be transferred to the user computing device.

3. The method of claim 1, additionally comprising providing information to an email program with information for notifying the user via an email that the selected medical data has been transmitted to the user computing device.

4. The method of claim 1, wherein the user-specific rules include criteria for selecting medical data for transfer to the user computing device based on one or more modality types of respective medical data, such that only medical data including images and/or information associated with the one or more modality types is selected.

5. The method of claim 1, wherein the user-specific rules include criteria for selecting medical data for transfer to the user computing device based on one or more image types of respective medical data, such that only medical data including images and/or information associated with the one or more image type is selected.

6. The method of claim 1, further comprising initiating transfer of secondary medical data of a same patient indicated in the selected medical data regardless of whether the secondary medical data has been marked as read.

7. The method of claim 1, further comprising:
   in response to determining that the user is not qualified to mark any medical data as read, allowing transfer of only medical data that is already marked as read to the user computing device.

8. The method of claim 1, further comprising:
   in response to determining that the user is not qualified to mark certain medical data as read, allowing the certain medical data to be transferred to the user computing system and not allowing the user to mark the certain medical data as read.

9. A system for retrieving medical data, the system comprising:
   a central processing unit; and
   an application module executing on the central processing unit, wherein the application module is configured to:
      receive user-specific rules, at least one of the user-specific rules indicating a required status of medical data, wherein the possible statuses of medical data include at least read and unread, wherein the read status indicates that a qualified user has completed review and evaluation of corresponding medical data, wherein users are determined to be qualified to provide read statuses in accordance with stored authorization information comprising user-specific and/or group-specific rights of users to provide read statuses wherein rights to provide read statuses vary based on at least job titles of respective users;
      determine a time period at which medical data should be retrieved from one or more medical data storage devices;
      periodically select at each interval of the time period medical data satisfying the received user-specific rules; and
      periodically retrieve the selected medical data from one or more medical data storage devices.

10. The system of claim 9, wherein the one or more types of user-specific rules that are receivable is determined based upon an access restriction of the user.

11. The system of claim 9, additionally comprising notifying a user that the selected medical data has been transmitted to a first computer.

12. The system of claim 9, wherein the user-specific rules include a modality type.

13. The system of claim 9, wherein the user-specific rules include an image type.

14. The system of claim 9, wherein the application module is further configured to transmit retrieved selected medical data to one or more computing devices associated with the user specific rules.

15. An article of manufacture including a computer-readable medium having instructions stored thereon that, in response to execution by a computing device, cause the computing device to perform operations comprising:
   determining qualifications of a user of the computing device to mark medical data as read based on at least their respective roles. wherein respective users have varying rights to mark medical data as read, and wherein marking medical data as read indicates that the user has completed observation of the respective medical data for purposes of creating a medical report;
   receiving filter criteria from the user, wherein the filter criteria includes at least a read status criteria, wherein at least some of the medical data are associated with respective read status indicators, the read status indicators indicating either that a user has completed observation and evaluation of corresponding medical data or that an indication that the user has completed observation and evaluation of corresponding medical data has not been received;
   selecting medical data satisfying the received filter criteria including the read status criteria;
   initiating transmission of the selected medical data from one or more storage devices to the computing device; and
   providing a notification to the user that the selected medical data has been transmitted to the computing device.

16. The computer-readable medium of claim 15, wherein one of the filter criteria indicates that only medical data assigned to the user is selected for transmission.

17. The computer-readable medium of claim 15, wherein one of the filter criteria indicates that only medical data that has been marked as read is selected for transmission.

18. The computer-readable medium of claim 15, wherein the qualifications of the user indicate that the user is not qualified to mark medical data as read.

19. The computer-readable medium of claim 18, wherein in response to the determined qualifications of the user, said selecting is limited to medical data that is marked as read.

20. The computer-readable medium of claim 15, wherein the selected medical data is transmitted via the Internet.

21. A method of retrieving medical data, the method comprising:
   receiving at a computing system user-specific rules indicating one or more attributes of respective medical data, the attributes including a read attribute having one of at least two values including a first value indicating that a user that is qualified to generate a report associated with the medical data has completed review of the corresponding medical data and a second value indicating that a user that is qualified to generate a report associated with the medical data has not completed review of the corresponding medical data, wherein users are determined to be qualified to change read attributes of respective medical data in accordance with stored authorization information comprising user-specific and/or group-specific rights of users to change read attributes of respective medical data; wherein users are assigned varying right to change read attributes based on respective roles of users;
   accessing at the computing system schedule information defining a schedule for checking for medical data stored on one or more storage device that matches the user-specific rules;
   periodically receiving at the computing system, medical data satisfying the user-specific rules, wherein any medical data satisfying the user-specific rules is received by the computing system at a time or interval indicated in the schedule information; and
   initiating transmitting of an electronic message to at least one user of the computing system via an electronic messaging program, wherein the electronic message indicates that medical data satisfying the user-specific rules has been received by the computing system.

22. The method of claim 21, wherein one or more types of user-specific rules that are receivable is determined based upon an access restrictions associated with the user.

23. The method of claim 21, further comprising transmitting the user-specific rules and the schedule information to a second computing system that initiates searches of the one or more storage devices or one or more indices of the storage devices according to the schedule information.

24. The method of claim 21, further comprising initiating execution of a software application in response to receiving medical data satisfying the user-specific rules.

25. The method of claim 24, wherein the software application comprises an image viewing software application.

26. The method of claim 21, further comprising, in response to receiving medical data at the computing system, initiating transmission of an electronic message to a user of the computing system indicating that medical data matching the user-specific rules has been received at the computing system.

27. The method of claim 26, wherein the electronic message comprises an e-mail message.

28. The method of claim 21, further comprising, in response to receiving medical data at the computing system, displaying on a display device of the computing system a user interface that allows the user to indicate whether respective medical images of the received medical data have been reviewed by the user.

29. The method of claim 28, further comprising transmitting indications that the user has reviewed respective medical images of the received medical data in response to receiving indications from the user via the user interface.

30. A system for retrieving medical data, the system comprising:
   a central processing unit; and
   an application module executing on the central processing unit, wherein the application module
      receives user-specific rules from a remote computer,
      intermittently selects medical data satisfying the received user-specific rules, wherein at least one of the user-specific rules indicates a required exam status selected from a group of exam statuses including at least read and unread, such that only medical data associated with the required exam status is selected, wherein a read exam status indicates that a user has completed observation of the medical data for purposes of creating a medical report, wherein users are determined to be qualified to change exam statuses of respective medical data to read in accordance with stored authorization information indicating varying rights for users and/or groups of users to change exam statuses based on at least respective roles of users and/or groups of users; and
      retrieves the selected medical data via a network.

31. The system of claim 30, wherein the user-specific rules indicate a required exam status of read, such that only medical data having a read exam status are selected.

32. The system of claim 30, wherein the user-specific rules indicate a required exam status of unread, such that only medical data having an unread exam status are selected.

33. The system of claim 30, wherein the user-specific rules indicate a required exam status of read or unread, such that medical data having either a read exam status or an unread exam status are selected.

* * * * *

UNITED STATES PATENT AND TRADEMARK OFFICE
CERTIFICATE OF CORRECTION

| | | |
|---|---|---|
| PATENT NO. | : 7,970,625 B2 | Page 1 of 1 |
| APPLICATION NO. | : 11/265979 | |
| DATED | : June 28, 2011 | |
| INVENTOR(S) | : Murray A. Reicher et al. | |

It is certified that error appears in the above-identified patent and that said Letters Patent is hereby corrected as shown below:

At Column 10, Line 39, in Claim 9 after "wherein" please delete "the".

At Column 10, Line 58, in Claim 10 after "wherein" please delete "the".

At Column 11, Line 11, in Claim 15 please delete "roles." and insert therefore, --roles,--.

At Column 11, Line 66, in Claim 21 please delete "right" and insert therefore, --rights--.

Signed and Sealed this

Thirteenth Day of December, 2011

David J. Kappos
*Director of the United States Patent and Trademark Office*